(12) United States Patent
Kingston et al.

(10) Patent No.: US 9,091,864 B2
(45) Date of Patent: Jul. 28, 2015

(54) SYSTEM AND METHOD OF CALCULATING VISUAL PERFORMANCE OF AN OPHTHALMIC OPTICAL CORRECTION USING SIMULATION OF IMAGING BY A POPULATION OF EYE OPTICAL SYSTEMS

(71) Applicant: Bausch & Lomb Incorporated, Rochester, NY (US)

(72) Inventors: Amanda C. Kingston, Rochester, NY (US); Paul D. Ludington, Brockport, NY (US); Richard Potvin, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 251 days.

(21) Appl. No.: 13/670,968

(22) Filed: Nov. 7, 2012

(65) Prior Publication Data
US 2014/0125954 A1 May 8, 2014

(51) Int. Cl.
*A61B 3/00* (2006.01)
*G02C 7/02* (2006.01)
*A61F 2/16* (2006.01)

(52) U.S. Cl.
CPC .. *G02C 7/028* (2013.01); *A61F 2/16* (2013.01)

(58) Field of Classification Search
USPC ......................................................... 351/246
See application file for complete search history.

(56) References Cited

U.S. PATENT DOCUMENTS

| 7,077,522 | B2 | 7/2006 | Williams |
|---|---|---|---|
| 7,357,509 | B2 | 4/2008 | Williams et al. |
| 2003/0199858 | A1 | 10/2003 | Schelonka |
| 2005/0254006 | A1 | 11/2005 | Dai et al. |
| 2011/0270596 | A1 | 11/2011 | Weeber |
| 2011/0279774 | A1 | 11/2011 | Dai |
| 2013/0308094 | A1 | 11/2013 | Mohan et al. |

FOREIGN PATENT DOCUMENTS

EP 1857077 A1 11/2007

OTHER PUBLICATIONS

Partial International Search Report for PCT/US2013/067171, received Dec. 12, 2013 (3 pages).
International Search Report and Written Opinion of the International Searching Authority in corresponding International Application No. PCT/US2013/067171, completed Apr. 15, 2014 (15 pages).
Marsack, et al.: Metrics of optical quality derived from wave aberrations predict visual performance Journal of Vision (2004) 4, 322-328.
Written Opinion of the International Preliminary Examining Authority, mailed Nov. 12, 2014 (8 pages).
Thibos et al, "Metrics of Optical Quality of the Eye", ARVO, Jan. 2, 2003, pp. 1-15.

*Primary Examiner* — Jack Dinh
(74) *Attorney, Agent, or Firm* — Toan P. Vo

(57) ABSTRACT

A method of calculating clinical performance of an ophthalmic optical correction using simulation by imaging a series of objects of different sizes by each of a plurality of eye optical systems, each of the eye optical systems including the ophthalmic optical correction, the method comprising A.) at an object distance, calculating a set of indicia of image quality, each indicium of the set of indicia corresponding to an object in the series of objects when it is imaged by a given one of the plurality of eye optical systems, B.) at the object distance, comparing the set of indicia to a threshold to determine a just-discernable object size for the given one of the plurality of eye optical systems, and C.) repeating steps A and B for each eye optical system in the plurality of eye optical systems.

26 Claims, 4 Drawing Sheets

SYSTEM AND METHOD OF CALCULATING VISUAL PERFORMANCE OF AN OPHTHALMIC OPTICAL CORRECTION USING SIMULATION OF IMAGING BY A POPULATION OF EYE OPTICAL SYSTEMS

FIELD OF INVENTION

The present invention relates to systems and methods for calculating visual performance of an ophthalmic optical correction, and more particularly to systems and methods for calculating visual performance of an ophthalmic optical correction using simulation of imaging by a population of eye optical systems.

BACKGROUND OF THE INVENTION

Clinical studies of ophthalmic lenses and other ophthalmic corrections are expensive and time consuming endeavors. Numerous efforts have been made to calculate visual performance using computer simulation to supplement clinical studies, yet there remains a need for a more versatile and/or accurate method of calculation for determining visual performance.

SUMMARY

Aspects of the present invention are directed to a method of calculating clinical performance of an ophthalmic optical correction using simulation by imaging a series of objects of different sizes by each of a plurality of eye optical systems. Each of the eye optical systems includes the ophthalmic optical correction. The method comprises A) at an object distance, calculating a set of indicia of image quality, each indicium of the set of indicia corresponding to an object in the series of objects when it is imaged by a given one of the plurality of eye optical systems, B) at the object distance, comparing the set of indicia to a threshold to determine a just-discernable object size for the given one of the plurality of eye optical systems and C) repeating steps A and B for each eye optical system in the plurality of eye optical systems.

In some embodiments, the ophthalmic optical correction comprises use of an ophthalmic lens.

The method may further comprise modifying an ophthalmic optical correction to include features of the ophthalmic optical correction based on steps A, B and C. The method may further comprise selecting an ophthalmic optical correction for use based on steps A, B and C.

The set of indicia of image quality may comprise an indication of resolution. In some embodiments, the set of indicia of image quality comprises substantially only resolution information.

The set of indicia of image quality may comprise an indication of contrast. In some embodiments, the set of indicia of image quality comprises substantially only contrast information.

In some embodiments, the set of indicia of image quality comprises resolution information and contrast information.

The steps A, B and C may be repeated for a plurality of object distances.

In some embodiments, the step of calculating a set of indicia of image quality comprises, for at least one of the plurality of object distances, calculating indicia of image quality for only a subset of the series of objects of different sizes.

In some embodiments, the step of calculating a set of indicia of image quality comprises, for at least one of the eye optical systems, calculating using different anatomical parameters for objects at different distances of the plurality of object distances.

The series of objects of different sizes may consist of a series of same letters of different sizes.

In some embodiments, step A may comprise, for an object in the series of objects, combining two or more image quality metrics, a first of the metrics providing a greater amount of resolution information and a second of the metrics providing a greater amount of contrast information. In some embodiments, the combining is achieved by multiplying the first of the metrics and the second of the metric together.

In some embodiments, the first metric contains substantially only resolution information. In some embodiments, the second metric contains substantially only contrast information.

In some embodiments, step D) comprises converting the just-discernible object sizes for each eye optical system to anticipated, clinical, just-resolvable object sizes using a linear mapping. In other embodiments, the method further comprises a step of converting the just-discernible object sizes for each eye optical system to anticipated, clinical, just-resolvable object sizes using a non-linear mapping.

The method may comprise calculating the set of indicia of image quality at only one object distance for each eye optical system.

Step A may be performed by optical design software. In some embodiments, step A is performed by an adaptive optical system.

The method may further comprising a step D) calculating a threshold, the step comprising i. at an object distance, for each eye optical system, clinically measuring a smallest resolvable object size, resulting in a clinical series of data, ii. for each eye optical system, calculating an indicium of image quality for each object size, at each distance, iii. determining a first series of just-resolvable-object size at each distance for each eye optical system using a first presumed threshold, iv. determining a first correlation factor between the first series and the clinical series of data, v. determining a second series of just-resolvable-object size at each distance for each eye optical system using a second presumed threshold, vi. determining a second correlation factor between the second series and the clinical series of data, and vii. selecting as the threshold the first presumed threshold if the first correlation factor is greater than the second correlation factor, and the second presumed threshold if the second correlation factor is greater than the first correlation factor.

In some embodiments, at least one of the first correlation factor and second correlation factor is calculated using a linear fitting curve. In some embodiments, at least one the first correlation factor and second correlation factor is calculated using a non-linear fitting curve.

In some embodiments, at least one of steps i. and ii. is repeated for multiple object distances.

The methods described herein may be performed by a suitably programmed processor, and may exist as instructions on a computer readable medium.

The term "ophthalmic optical correction" refers to an ophthalmic lens used with an eye, an optical feature of an eye that has been refractively corrected or other ophthalmically modified features of an eye optical system. For example, an optical feature of an eye that has been refractively corrected may include a crystalline lens or cornea that has been reshaped or otherwise optically modified using a mechanical or optical technique (e.g., LASIK or change of index of refraction).

The term "ophthalmic lens" refers to any artificial lens for use with an eye (e.g., a spectacle, a contact lens, an intraocular lens, a corneal inlay or a corneal onlay). An ophthalmic lens may comprise one or more optical elements. An ophthalmic lens may be multifocal or single vision. An ophthalmic lens may be refractive and/or diffractive. An ophthalmic lens may be monofocal or multifocal (e.g., bifocal or trifocal).

The term "population of eye optical systems" is used herein to refer to a plurality of optical systems, each optical system including the optical portion of an eye.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Aspects of the present invention are directed towards attaining a prediction of clinical, visual performance of an ophthalmic optical correction by simulation of use of the ophthalmic optical correction in a population of eye optical systems with which the correction is to be used. It should be understood that an eye optical system generates a retinal image.

Figure 1:
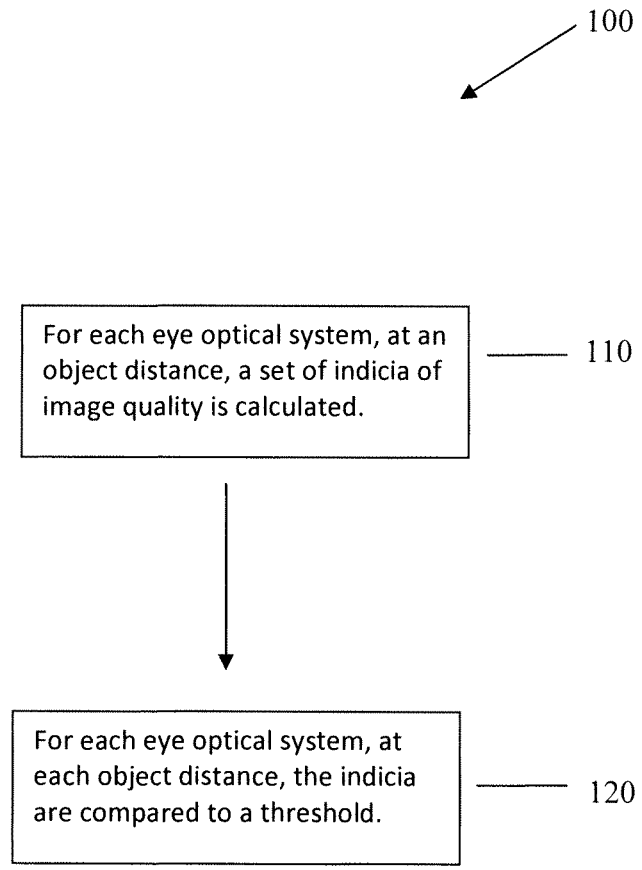
FIG. 1 is a flow chart showing an example of a method of calculating clinical performance of a ophthalmic optical correction according to aspects of the present invention.

An aspect of the invention is directed to a method of calculating clinical performance of an ophthalmic optical correction using simulation by imaging a series of objects of different sizes by each of a plurality of eye optical systems, each of the eye optical systems including the ophthalmic optical correction. FIG. 1 is a flow chart showing an example of such a method 100. An eye optical system including the ophthalmic optical correction is also referred to herein as a modified eye optical system.

The ophthalmic optical correction is located in each optical system in a manner consistent with the anticipated use. For example, a contact lens is located in contact with the outer surface of the cornea of the eye, an intraocular lens is located in the eye at an appropriate location with the eye's natural lens being omitted or remaining in place, and/or a cornea is appropriately modified to correspond to a refractive procedure.

Simulation of imaging by an eye can be achieved using any suitable technique. For example, optical and anatomical parameters can be entered into an optical design software system (e.g., Zemax, Code V or Oslo) to produce an eye model corresponding to a modified eye optical system. Simulated imaging may be achieved, for example, (1) by tracing rays from a given object through the eye model and/or (2) by obtaining a point spread function for the model and convolving the point spread function with the object. The simulated imaging results in the generation of a modified eye optical system output (e.g., a retinal image). Simulated imaging may be repeated for each object size or for a subset of the series of objects. The sizes of the objects of different sizes may correspond to typical logMAR or Snellen eye chart sizes or using any other suitable selection technique. The inventors have found that a series of a same letter of different sizes is effective (e.g., a series of O's, E's or X's).

Each object in the series (i.e., the series of objects of different sizes) may be imaged at each of a plurality of object distances. At one or more of the distances, a subset of the series of objects in the series may be imaged. Object distances may range from near distance (e.g., 4 diopters (i.e., 25 cm) to a far distance of infinity) or a subset thereof. In some instances, an ophthalmic optical correction may be evaluated at a single distance, most commonly the far distance (i.e., effectively an infinite object distance). A technique using only the far distance is most commonly used with ophthalmic optical corrections to be used by non-presbyopic individuals.

For example, for each eye, the following optical and anatomical parameters may be measured to produce the eye model: ocular aberrations, pupil diameter, corneal curvature, corneal thickness, anterior chamber depth and axial length. For any parameters that vary as a function of object location (e.g., ocular aberrations, pupil diameter), a value may be measured for each object distance and used to calculate the indicia of image quality set forth below.

To determine visual performance, for each eye optical system, at an object distance, a set of indicia of image quality is calculated (step 110). Each indicium of the set of indicia corresponds to a different object in the series of objects and is indicative of the image quality when the object is imaged by the eye optical system onto a retina. Image quality can comprise a measure of resolution and/or contrast. For example, a resolution indicium can be calculated using a cross-correlation algorithm of the output image of the modified eye optical system with a perfect representation of the object at the proper magnification letter. Other image quality metrics may include measures of resolution and/or contrast such as modulation transfer function (MTF) (where low frequencies are generally associated with a measure of contrast and high frequencies are generally associated with a measure of resolution), Strehl ratio, visual Strehl optical transfer function (VSOTF) or a combination of these indicia of image quality. As stated above, at each distance (e.g., at 9 distances), an indicia is calculated for each object in the series of objects of different sizes or for a subset of objects in the series. Also, as stated above, for a given eye, different anatomical parameters may be used to calculate indicia at different object distances.

For each modified eye optical system, at each object distance, the indicia are compared to a threshold to determine a just-discernible object size (step 120). Calculation of a threshold is discussed in greater detail below. The smallest object that results in an indicium greater than the threshold is the just-discernible object size.

Figure 2:
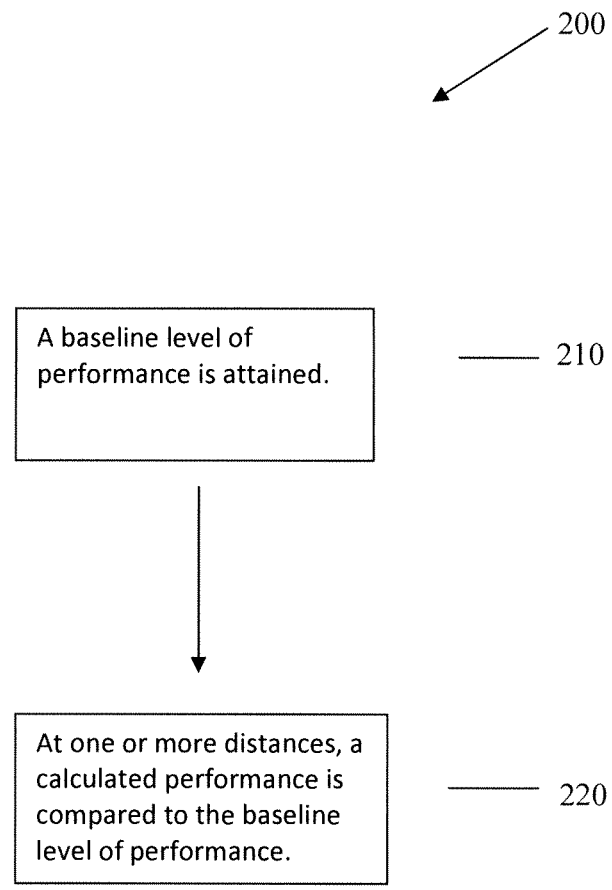
FIG. 2 is a flow chart showing another example of a method that includes further steps that may be used to calculate visual performance of an ophthalmic optical correction according to aspects of the present invention.

To further determine a visual performance of an ophthalmic optical correction, a baseline level of performance may be attained. FIG. 2 is a flow chart showing a method 200 including further steps that may be used to determine visual performance. At step 210, the baseline level of performance may be attained by (1) calculating or clinically measuring a performance of a baseline eye optical system that includes a baseline ophthalmic optical correction (i.e., any ophthalmic optical correction that is different than the ophthalmic optical correction) or (2) calculating or clinically measuring a performance of a baseline eye system without an ophthalmic optical correction. For the baseline eye optical system, an indicia of image quality is calculated or measured at each distance (e.g., 9 distances) for the plurality of objects of different sizes to determine the object size that is just discernible (i.e., having an image metric at or greater than the threshold).

At step 220, one or more distances, the calculated performance of the ophthalmic optical correction in an eye system is compared to performance of the baseline ophthalmic optical correction in an eye system in the following manner. From (1) the performance results for the baseline eye optical system, (2) the calculated results for the modified eye optical system including the ophthalmic optical correction under test, and (3) a given set of objective criteria, it is possible to establish a measure of how well the modified eye optical system that includes the ophthalmic optical correction under test performed as compared to the baseline eye system. For example, by comparing the results for the ophthalmic optical correction under test and the baseline ophthalmic optical correction, it can be determined what percentage of wearers would prefer the ophthalmic optical correction under test based on the set of criteria (e.g., for a percentage of wearers the correction is better at a given distance or achieves better performance based on a weighted measure of several distances).

The criteria can include a comparison of the modified eye system and the baseline eye system using values from individual eye systems or averages across a population. The criteria, also, may include values from individual distances or use an average performance at two or more distances, with different distances having the same or different weightings. It will be appreciated that performance at the far distance is usually given the greatest weighting. Criteria may include only individual values or only averages, or any combination thereof.

After performing the above calculations to determine performance, the ophthalmic optical correction under test may be modified (or another ophthalmic optical correction may be modified) based on calculated performance to include or omit features of the ophthalmic optical correction. For example, modification can be performed if the calculated performance has a selected value (e.g., above, below or at a selected threshold). For example, features of a lens can be implemented into a lens design after determining that the performance was adequate or determining that the calculated performance was superior to the baseline lens.

Also, after performing the above calculations to determine performance, it is possible to compare the calculated clinical performance of the ophthalmic optical correction under test to a clinical performance (calculated or clinically measured) of a second ophthalmic optical correction and to select the first ophthalmic optical correction for use or the second ophthalmic optical correction. For example, the selection can be made depending on their relative performances.

Also, if performance of only a single ophthalmic optical correction is calculated, the ophthalmic optical correction may be selected for use based on the calculated performance if the indication of clinical performance meets selected criteria (e.g., performance was above, below or at a selected threshold).

As discussed above, simulation of imaging by a population of eyes can be achieved by various techniques. An alternative technique to computer simulation using a software system is the use of an adaptive optic system to simulate the performance of the eyes including an ophthalmic optical correction. The adaptive portion of the optic system may include a MEMS, voice coil, silicon light modulator, liquid crystal component that is refractive or reflective to simulate aberrations of the eye. The optic system may include a pupil having a variable aperture. A simulated retinal image for a simulated eye optical system including the ophthalmic optical correction can be captured from the adaptive optical system on an opto-electronic transducer such as a CCD. The images captured and subsequent processing of the images is the same as described above.

Calculation of Threshold

Figure 3:
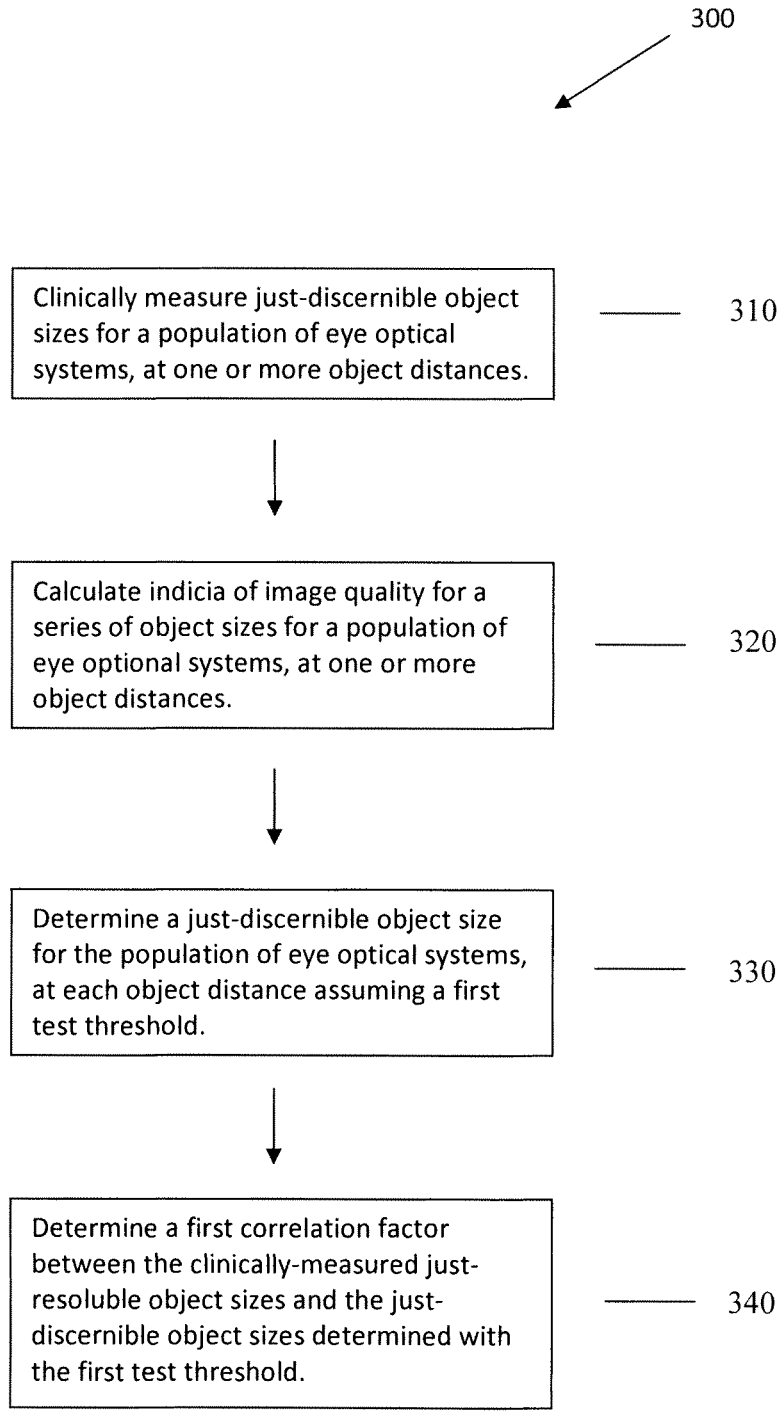
FIG. 3 is a flow chart showing an example of a technique for establishing a threshold value according to aspects of the present invention.
Figure 3:
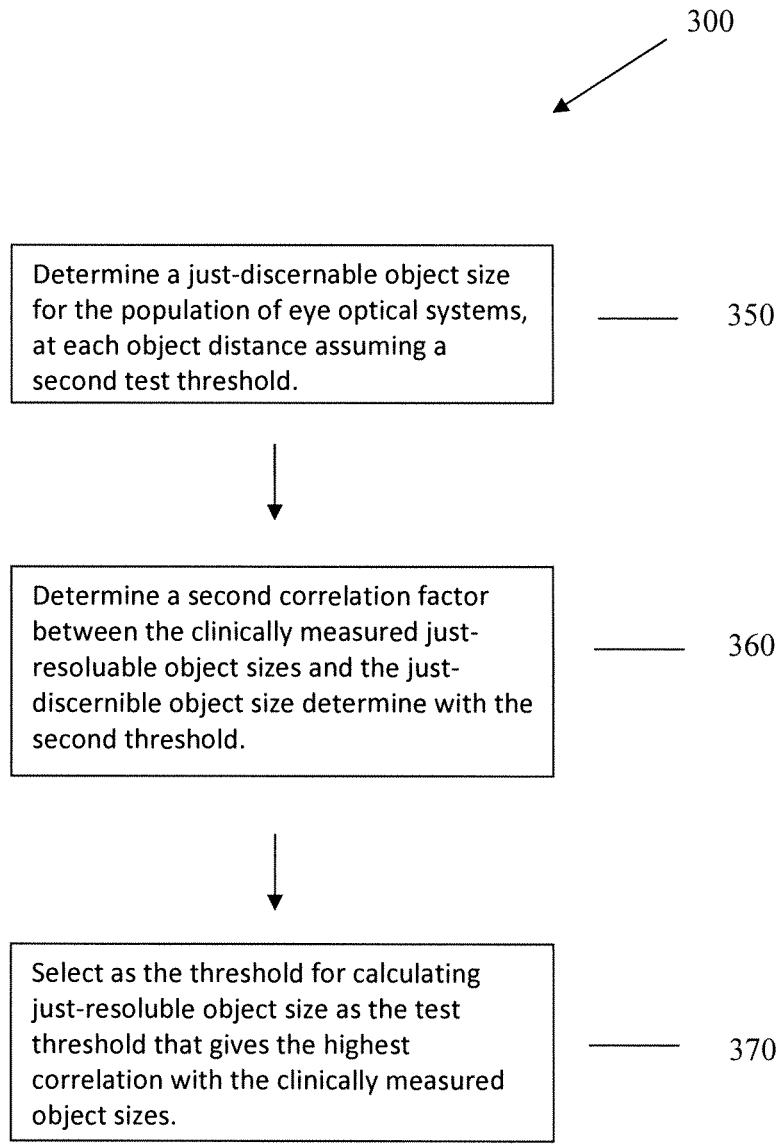

As set forth above, a calculated level of performance at a particular distance, for a modified eye system, can be determined by comparing the calculated indicia of image quality to a threshold and taking as the just-resolvable object size the smallest object size that has a calculated indicia of image quality that is greater than the threshold. An example of a technique for establishing a threshold value is set forth below (FIG. 3); however, any suitable technique can be used.

Firstly, it should be appreciated that, by establishing an appropriate threshold, a relationship between the calculated results and the actual, clinical performance can be established.

To determine a threshold, a population of eye optical systems (e.g., 90 patients, 180 eyes) is assembled. Ideally the patients' eyes are representative of the population of patients/consumers who are intended to wear the ophthalmic lens and can include sub-populations of patients, each sub-population including a selected number of patients with a given characteristic or condition. For example, a selected number can be advanced presbyopes, a selected number can be early presbyopes, and a selected number could be non-presbyopes.

A subjective, clinical measure of visual acuity is measured at one or more object distances for each eye optical system. For example, a logMAR or a Snellen chart is used in a conventional manner (i.e., using a series of objects of different sizes) to obtain a smallest resolved object size (step 310). A chart for clinical use may include a series of a same letter of different sizes. Accordingly, if nine object distances are used, each eye has associated with it nine logMAR or Snellen values. The collection of clinically measured, just-discernable object sizes is referred to herein as a clinical series of data.

Also, during the subjective, clinical measurements, for each eye, optical and anatomical parameters, as set forth above, are measured. The anatomical parameters may include any appropriate anatomical data to account for variations of the optical and anatomical parameters as a function of object distance. For ocular aberrations measurements, it is typically advantageous if they are measured while the patient fixates on the smallest resolvable object at a particular object distance. The parameters are used to produce eye models corresponding to each eye in the population by entering optical and anatomical parameters into an optical design software system (e.g., Zemax, Code V) or using adaptive optics as set forth above. Eyes included in the population may be aided by a lens (i.e., a lens in addition to the ophthalmic optical correction under test) or not provided that any such aid is included in the model of the eye. A simulated population of eyes is thereby generated.

After entering the data, for each eye, at each distance, a simulated series of object sizes is input into an eye model, the simulated series being a representation of the series of objects used in the subjective, clinical test. For each eye, and at each distance, an indicium of image quality is calculated for each object size (or a suitable subset of object sizes) (step 320).

Calculated performance for each eye is determined by assuming a first, test threshold value for the just-resolvable object size for each eye at each distance (step 330). The clinical results for each eye at all object distances, results in a series of just-resolvable object sizes. The resulting just-resolvable object sizes for all eyes and all distance are compared to the subjective, clinical results. A correlation factor is determined for the first, test threshold (step 340). For example, the correlation is determined by assuming a linear relationship between the data.

Next, calculated outputs for each eye are determined by assuming a second test threshold value for determining the just-resolvable object size (step 350). The resulting object sizes for all eyes and all distances are compared to the subjective, clinical results. A correlation factor is determined for the second, test threshold (step 360). The process is repeated for any number of additional thresholds.

The appropriate threshold is selected as the test threshold that gives the highest correlation between the calculated and subjective, clinically-observed just-resolved object sizes (step 370).

It will be appreciated that the selected linear relationship may not extend through the data such that a given calculated just-resolvable object size (e.g., 0.2 logMAR) corresponds to a calculated object size (0.2 logMAR). In fact, the inventors have determined that the relationship between the calculated just-resolvable and clinically observed just-resolvable object size is typically non-linear (e.g., a polynomial or other fitting curve provides a better correlation). The non-linear fitting curve compensates for the fact that, independent of object distance, patient visual performance is typically better than expected (i.e., better than calculations would indicate) for larger letters and worse than expected for smaller letters.

It will be appreciated that once the correction between calculated just-resolvable object sizes and clinically-observed just-resolvable object sizes is determined, it is possible to convert (i.e., map) a subsequently calculated just-resolvable object sizes for any ophthalmic optical correction to anticipated clinical just-resolvable object sizes for any or all eye optical systems in the population.

Additional Techniques for Calculating Indicia of Image Quality

It will be appreciated that the accuracy of the calculated just-resolvable object size could be improved if it were possible to improve the correlation between calculated just-resolvable object size and the clinically-observed just-resolvable object size. To this end the inventors have determined that, in some instances, it is desirable to avoid a situation in which a disproportionate amount of information about contrast or resolution is included in an indicium or set of indicia. Accordingly, at each distance, for each object size, aspects of the present invention include, calculating a given indicium of image quality by combining two or more image quality metrics, at least one of said metrics providing a greater amount of (or substantially only) information about contrast of a retinal image and another providing a greater amount of (or substantially only) information about resolution of a retinal image, to obtain an indicium of image quality. The step of combining may be repeated for each object size at a given distance or only the object size that is just-resolvable. It will be appreciated that an appropriate amount of resolution and contrast is determined by further including an amount resolution information or contrast information and determining if the correlation between calculated results and clinical results is increased or decreased. Typically, the combining is achieved by multiplying the indicia including a greater amount resolution information and the indicia including a greater amount contrast information; however, other combinations may be used such as addition with or without a weighting factor.

For example, in some embodiments, for each of the objects in the series, an indicia containing substantially only resolution information is calculated for each eye output (i.e., retinal image), for example, using a cross-correlation technique as set forth above; and for each of the objects in the series, an indicia containing substantially only contrast information is calculated for each eye output. The two indicia containing substantially only resolution information is combined with the indicia containing substantially only contrast information to form the indicia of image quality.

The indicia containing substantially only contrast may be any suitable measure of contrast indicative of the image contrast when the object is imaged by the optical system. Image contrast can be calculated in many ways, for example, by calculating a peak intensity level in a light region of the object image and a minimum intensity level in a dark region of the object image and using the following equation $$\text{Contrast} = \frac{\text{Intensity}_{max} - \text{Intensity}_{min}}{\text{Intensity}_{max} + \text{Intensity}_{min}}$$

where $\text{Intensity}_{max}$ and $\text{Intensity}_{min}$ are indications (e.g., electronic detector output) of signal strength in a region of maximum intensity in the image and in a region of minimum intensisty in the image, respectively. For example, signal strength may be measured as a number of rays to hit specific areas in the image.

It will be appreciated that an indicium of image quality including two or more metrics can be used for calculation of the threshold (as set forth above) and for calculation of lens performance (as set forth above).

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method of calculating clinical performance of an ophthalmic optical correction using simulation by imaging a series of objects of different sizes by each of a plurality of eye optical systems, the method comprising:
   initially, determining a threshold, including: clinically measuring visual acuity, anatomical parameters and optical parameters of a population of eyes; providing an eye optical system corresponding to each eye in said population based on said parameters;
   and correlating clinically measured just-resolvable object sizes and just-resolvable object sizes calculated by the corresponding eye optical system; and subsequently:
   A. at an object distance, calculating a set of indicia of image quality, each indicium of the set of indicia corresponding to an object in the series of objects when it is imaged by a given one of the plurality of eye optical systems that include the ophthalmic optical correction;
   B. at the object distance, comparing the set of indicia to said threshold to determine a just-resolvable object size for the given one of the plurality of eye optical systems that include the ophthalmic optical correction; and
   C. repeating steps A and B for each eye optical system in the plurality of eye optical systems.

2. The method of claim 1, wherein the ophthalmic optical correction comprises use of an ophthalmic lens.

3. The method of claim 1, further comprising modifying an ophthalmic optical correction to include features of the ophthalmic optical correction based on steps A, B and C.

4. The method of claim 1, further comprising selecting an ophthalmic optical correction for use based on steps A, B and C.

5. The method of claim 1, wherein the set of indicia of image quality comprises an indication of resolution.

6. The method of claim 1, wherein the set of indicia of image quality comprises substantially only resolution information.

7. The method of claim 1, wherein the set of indicia of image quality comprises an indication of contrast.

8. The method of claim 1, wherein the set of indicia of image quality comprises substantially only contrast information.

9. The method of claim 1, wherein the set of indicia of image quality comprises resolution information and contrast information.

10. The method of claim 1, wherein steps A, B and C are repeated for a plurality of object distances.

11. The method of claim 10 wherein, the step of calculating a set of indicia of image quality comprises, for at least one of the plurality of object distances, calculating indicia of image quality for only a subset of the series of objects of different sizes.

12. The method of claim 10, wherein the step of calculating a set of indicia of image quality comprises, for at least one of the eye optical systems, calculating using different anatomical parameters for objects at different distances of the plurality of object distances.

13. The method of claim 1, wherein the series of objects of different sizes consists of a series of same letters of different sizes.

14. The method of claim 1, wherein step A comprises, for an object in the series of objects, combining two or more image quality metrics, a first of the metrics providing a greater amount of resolution information and a second of the metrics providing a greater amount of contrast information.

15. The method of claim 14, wherein the combining is achieved by multiplying the first of the metrics and the second of the metric together.

16. The method of claim 14, wherein the first metric contains substantially only resolution information.

17. The method of claim 14, wherein the second metric contains substantially only contrast information.

18. The method of claim 1, further comprising a step of converting the just-resolvable object sizes for each eye optical system to anticipated, clinical, just-resolvable object sizes using a linear mapping.

19. The method of claim 1, further comprising a step of converting the just-resolvable object sizes for each eye optical system to anticipated, clinical, just-resolvable object sizes using a non-linear mapping.

20. The method of claim 1, wherein the method comprises calculating the set of indicia of image quality at only one object distance for each eye optical system.

21. The method of claim 1, wherein step A. is performed by optical design software.

22. The method of claim 1, wherein step A is performed by an adaptive optical system.

23. The method of claim 1, wherein determining a threshold includes:
   i) At an object distance, for each eye, clinically measuring a smallest resolvable object size, resulting in a clinical series of data;
   ii) for each eye optical system, calculating an indicium of image quality for each object size, at each distance;
   iii) determining a first series of just-resolvable-object size at each distance for each eye optical system using a first presumed threshold;
   iv) determining a first correlation factor between the first series and the clinical series of data;
   v) determining a second series of just-resolvable-object size at each distance for each eye optical system using a second presumed threshold;
   vi) determining a second correlation factor between the second series and the clinical series of data; and
   vii) selecting as the threshold the first presumed threshold if the first correlation factor is greater than the second correlation factor, and the second presumed threshold if the second correlation factor is greater than the first correlation factor.

24. The method of claim 23, wherein at least one of the first correlation factor and second correlation factor is calculated using a linear fitting curve.

25. The method of claim 23, wherein at least one the first correlation factor and second correlation factor is calculated using a non-linear fitting curve.

26. The method of claim 23, wherein at least one of steps I. and ii. is repeated for multiple object distances.

* * * * *